United States Patent [19]

Appel et al.

[11] Patent Number: 5,118,874
[45] Date of Patent: Jun. 2, 1992

[54] PARTIALLY FLUORINATED BIPHENYLS, PROCESSES FOR THEIR PREPARATION AND THEIR USE

[75] Inventors: Wolfgang Appel, Kelkheim; Günter Siegemund, Hofheim, both of Fed. Rep. of Germany

[73] Assignee: Hoechst Aktiengesellschaft, Frankfurt am Main, Fed. Rep. of Germany

[21] Appl. No.: 717,910

[22] Filed: Jun. 20, 1991

[30] Foreign Application Priority Data

Jun. 25, 1990 [DE] Fed. Rep. of Germany ....... 4020184

[51] Int. Cl.⁵ .................... C07C 39/12; C07C 25/18
[52] U.S. Cl. ........................... 568/718; 528/312; 528/317; 568/717; 568/719; 568/775; 568/779; 570/126; 570/182; 570/183; 570/184; 570/185; 570/189
[58] Field of Search ............... 570/126, 182, 183, 184, 570/185, 189; 560/717; 568/718, 706, 775; 528/310, 312, 317; 252/648

[56] References Cited

U.S. PATENT DOCUMENTS 3,355,500  11/1967  Farah et al. ................. 568/585
3,825,534  7/1974   Weber et al. ................. 570/182
4,956,055  9/1990   Puckette ....................... 570/185

FOREIGN PATENT DOCUMENTS 0063874  11/1982  European Pat. Off. ........... 568/325
0126494  11/1984  European Pat. Off.
3739795  6/1989   Fed. Rep. of Germany ...... 568/585
63-199237  8/1988  Japan.

Primary Examiner—Werren B. Lone

[57] ABSTRACT

Compounds of the formula

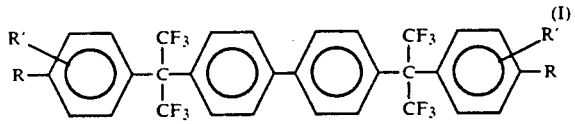

in which, independently of one another, each R is OH or lower alkyl having 1-4 carbon atoms and each R' is hydrogen or lower alkyl having 1-4 carbon atoms, are prepared by the condensation of partially fluorinated aromatic hydrocarbons in the presence of hydrogen fluoride or by the reductive coupling of partially fluorinated aromatic compounds. The compounds are used as a starting material for the preparation of partially fluorinated polycondensates.

21 Claims, No Drawings

PARTIALLY FLUORINATED BIPHENYLS, PROCESSES FOR THEIR PREPARATION AND THEIR USE

The invention relates to new, partially fluorinated biphenyls, processes for their preparation and their use as an intermediate for the synthesis of partially fluorinated monomers and partially fluorinated polycondensates.

Biphenyls containing 2 hexafluoroisopropyl groups having aminophenyl radicals are known as a curing component of epoxy resins for composite materials and as a component of polyimide composite materials (EP-B 0,126,494 and JP-A 63,199,237).

A process for the preparation of polyketones in the presence of fluoroalkanesulfonic acids is also described, in which aromatic diacid halides which, in accordance with a formula containing several variables, can also be based on partially fluorinated biphenyls are employed as one of the reactants (EP-A 0,063,874). In this regard acid halides are absolutely necessary for the acylation process; the corresponding free acids can therefore not be used.

Partially fluorinated diphenyl ethers which are prepared in the presence of hydrogen fluoride and are used as a component for the synthesis of monomers and polycondensates are also known (DE-A 3,739,795).

The invention accordingly provides compounds of the formula

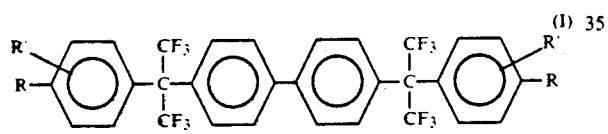

in which, independently of one another, each R is OH or lower alkyl having 1-4 carbon atoms and each R' is hydrogen or lower alkyl having 1-4 carbon atoms, alkyl being preferably $CH_3$, to processes for their preparation and to their use. In formula (I) the radical R' is preferably in the ortho-position relative to the radical R.

In general, the compounds according to the invention can be prepared by three different methods, specifically:

a) by condensation of one mole of a dicarbinol of the formula

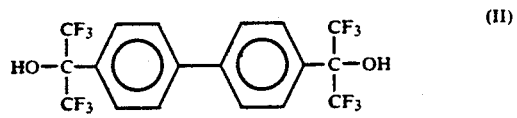

with at least 2 mol of a compound having the formula

in which R has the meaning mentioned above, or b) by condensation of at least 2 mol of a compound of the formula

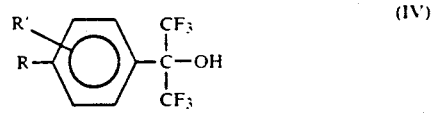

in which R has the meaning mentioned above, with one mole of biphenyl (V), in each case in the presence of hydrogen fluoride, or c) by the formation of the carbon-carbon bond between 2 identical partially fluorinated aromatic compounds of the formula

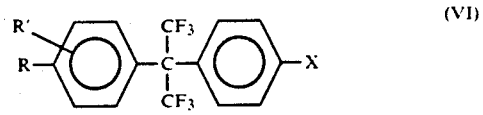

in which R has the meaning mentioned above, by a method which is known from the literature and which is suitable for the formation of aryl-aryl bonds, for example J. Org. Chem. 51, 2627 (1986). X is halogen, preferably chlorine. When this method of synthesis is used, in the special case where R is OH, it is necessary to protect the hydroxyl group before the formation of the aryl-aryl bond, for example by means of an acetyl group.

Compounds of the formula (II) employed in method a) are described in U.S. Pat. No. 3,355,500 and in J. Org. Chem. 30, (1965). Compounds of the formula (IV) which can be reacted by method b) to give the compounds according to the invention are also described in J. Org. Chem. 30, 998-1001 (1965).

Examples of aromatic substituted hydrocarbons of the formula (III) are phenyl compounds substituted by OH and/or alkyl radicals having 1-4 carbon toms, such as phenol, toluene, the various xylenes and cresols.

The reaction according to methods a) and b) is carried out at a temperature from 80° to 180° C., preferably 100° to 160° C.

A time of 20 to 90 hours, preferably 40 to 70 hours, is necessary for the reaction according to methods a) and b).

The molar ratio of the reactants employed is determined in the case of method a) by the ratio of the compound (II) to the compound (III) and, in method b), by the ratio of the biphenyl to the compound (IV); it is in each case at least 1:2, preferably 1:2.2 to 1:4.4.

The proportion of hydrogen fluoride required in the reaction for the preparation of the compounds according to the invention is related in the case of method a) to the compound (II); it is generally used in a molar ratio of 1:7 to 1:25, preferably 1:8 to 1:12. In the case of method b) the molar ratio of the compound (IV) to hydrogen fluoride is generally 1:6 to 1:15, preferably 1:8 to 1:12.

The reaction product is generally worked up by removing, as gas, the hydrogen fluoride from the reactor after the completion of the reaction at approx. 80° C. and by removing from the reactor, preferably at a temperature of 20°-30° C., the residue which remains, if appropriate after dilution with an organic solvent.

Suitable solvents which can be used for this are aliphatic hydrocarbons having 5 to 10 carbon atoms, aromatic hydrocarbons having 6 to 8 carbon atoms and monochlorinated or polychlorinated aliphatic hydrocarbons having 1 to 4 carbon atoms in the alkyl radical.

Examples of these are n-hexane, n-heptane, toluene, the various xylenes, methylene dichloride and chloroform, preferably toluene, methylene dichloride or chloroform.

Water is added to the crude mixture obtained, which is washed and separated off. In general, the purified products are obtained in the form of colorless crystals.

The reaction product can be purified further by being subjected to recrystallization from an organic solvent or by being extracted by stirring in organic solvents, preferably in isopropanol, methanol or 1-chloropropane.

The preparation of the compounds shown in formula (VI) can be effected by known methods from compounds of the formula (IV) and aryl halides.

The formation of the aryl-aryl bond between two components of the formula (VI) is carried out in a polar, aprotic solvent, such as dimethylacetamide or dimethylformamide, in the presence of a mixture of 1-10 mol %, preferably 3 to 6 mol %, of a nickel(II) salt, preferably $NiCl_2$ or $NiBr_2$, and 5-40 mol %, preferably 20 to 30 mol %, of an organic phosphorus(III) compound, preferably triphenylphosphine, and zinc powder in a ratio of 120-160 mol %, relative to the aryl halide employed.

The reaction is carried out in an inert gas atmosphere, particularly nitrogen or argon, at a temperature of 40° to 80° C.; the reaction takes 2 to 8 hours.

The solid fraction is filtered off and, after the addition of a water-immiscible solvent, for example a monochlorinated or polychlorinated aliphatic hydrocarbon having 1-4 carbon atoms in the alkyl radical, in particular methylene dichloride or chloroform, ethyl acetate or diethyl ether, the filtrate is washed several times with water. Separation of the phases takes place. After the organic phase has been dried, the solvent is distilled off and the residual product is purified by recrystallization.

The following are specific examples of novel partially fluorinated biphenyl derivatives embraced by the invention:

4,4'-bis-[2-(4-hydroxyphenyl)-hexafluoroisopropyl]-biphenyl 4,4'-bis-[2-(4-methylphenyl)-hexafluoroisopropyl]-biphenyl 4,4'-bis-[2-(3,4-dimethylphenyl)-hexafluoroisopropyl]-biphenyl The new compounds are used in particular for the preparation of monomers used as a component of partially fluorinated polycondensates, for example polyesters, polyamides and polyimides, such as have been described in the coterminous patent applications "Partially fluorinated tetracarboxylic acid and the dianhydride thereof, processes for their preparation and their use", DE-P 40 20 186.4, and "Partially fluorinated dicarboxylic acid and the acid chloride thereof, processes for their preparation and their use", DE-P 40 20 185.6.

EXAMPLES

1)
4,4'-Bis-2-(4-methylphenyl)-hexafluoroisopropyl]-biphenyl

Synthesis by method a)

A two-liter VA stirred autoclave (VA = chrome nickel steel) was charged with 302 g of 4,4'-bis-[hexafluoro-2-hydroxy-2-propyl]-biphenyl, 140 g of toluene and 300 g of anhydrous hydrogen fluoride, and was stirred for 64 hours at 140° C. After cooling to 80° C. the hydrogen fluoride was removed in the form of gas. After the addition of 200 ml of toluene, the product was removed from the autoclave, and the organic phase was washed several times with water and dried over $CaCl_2$. After the solvent had been removed by distillation, the solid residue was recrystallized from methanol. The yield was 212 g (54%) of product, melting point 167°-168° C.

Synthesis by method b)

A two-liter VA stirred autoclave was charged with 620 g of 2-(4-methylphenyl)-hexafluoropropan-2-ol, 154 g of biphenyl and 720 g of anhydrous hydrogen fluoride, and was stirred for 64 hours at 160° C. After the temperature had been reduced, the hydrogen fluoride was removed in the form of gas at 80° C. and, after the addition of 800 ml of toluene, the product was removed from the autoclave. The organic phase was washed several times with water and then dried over $CaCl_2$. After filtration and removal of the solvent, 478 g (75%) of product of melting point 168°-169° C. were obtained by recrystallizing the residue from 2000 ml of methanol.

| Analysis for $C_{32}H_{22}F_{12}$ | | |
|---|---|---|
| C % | H % | F % |
| calc.: 60.57 | 3.49 | 35.93 |
| found: 60.60 | 3.40 | 35.60 |

Synthesis by method c)

2.2 g of nickel(II) bromide, 15 g of triphenylphosphine and 20 g of zinc dust were initially placed in 150 ml of anhydrous, degassed dimethylacetamide under an atmosphere of nitrogen, and the mixture was stirred for 30 minutes at 40° C. 70 g of 2-(4-chlorophenyl)-2-(4-methylphenyl)-hexafluoropropane in 150 ml of anhydrous, degassed dimethylacetamide were added to this solution, and the mixture was stirred for 3 hours at 40°-50° C. The solid fraction was filtered off at 20°-30° C. and washed with 300 ml of ethyl acetate; the filtrate was washed several times with water, and the organic phase was dried over magnesium sulfate. The residue obtained after distilling off the solvent was recrystallized from methanol. The yield was 64 g (50.8%) of 4,4,-bis-[2-(4-methylphenyl)-hexafluoroisopropyl]-biphenyl of melting point 168°-169° C.

2)
4,4'-Bis-2-(4-hydroxyphenyl)-hexafluoroisopropyl]-biphenyl

Synthesis by method a)

A two-liter VA stirred autoclave was charged with 302 g of 4,4'-bis-[hexafluoro-2-hydroxy-2-propyl]-biphenyl, 140 g of phenol and 300 g of anhydrous hydrogen fluoride, and the mixture was stirred for 48 hours at 110° C. After cooling to 80° C. the hydrogen fluoride was removed by condensation. After the addition of methylene chloride, the product was removed from the autoclave and the organic phase was washed several times with water and dried over $CaCl_2$. After the removal of the solvent by distillation, the solid residue was purified by recrystallization from 4:1 methylene chloride/n-hexane. The yield was 221 g (55% of theory) of a solid, melting point 196°-198° C.

3)
4,4'-Bis-2-(3,4-dimethylphenyl)-hexafluoroisopropyl]-biphenyl

Synthesis by method b)

A two-liter VA stirred autoclave was charged with 598 g of 2-(3,4-dimethylphenyl)-hexafluoropropan-2-ol, 154 g of biphenyl and 720 g of anhydrous hydrogen fluoride, and the mixture was stirred for 70 hours at 150° C. After the temperature had been reduced to 80° C., the hydrogen fluoride was removed in the form of gas and, after the addition of 500 ml of toluene, the product was removed from the autoclave. The organic phase was washed several times with water and dried over CaCl₂, and the solvent was then removed by distillation. The residue was recrystallized from 1000 ml of isopropanol to which 20 g of active charcoal had been added. 385 g (58%) of product of melting point 164°–165° C. were obtained.

We claim:

1. A compound of the formula

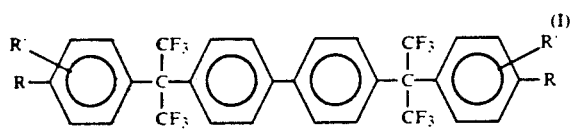

in which, independently of one another, each R is OH or lower alkyl having 1 to 4 carbon atoms, and each R' is hydrogen or lower alkyl having 1 to 4 carbon atoms.

2. 4,4'-Bis-[2-(4-hydroxyphenyl)-hexafluoroisopropyl]-biphenyl.

3. 4,4'-Bis-[2-(4-methylphenyl)-hexafluoroisopropyl]-biphenyl.

4. 4,4'-Bis-[2-(3,4-dimethylphenyl)-hexafluoroisopropyl]-biphenyl.

5. A process for the preparation of a compound of the formula

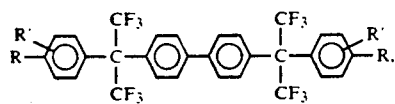

which comprises a) reacting a dicarbinol of the formula

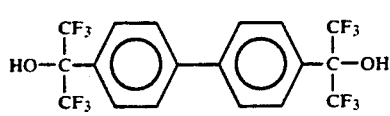

with an aromatic hydrocarbon of the formula

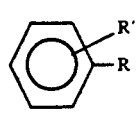

or b) reacting a fluorine compound of the formula

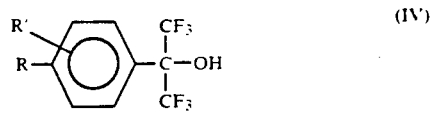

(IV')

with biphenyl (V), in which formulae R and R' have the meaning mentioned in formula (I), in the presence of hydrogen fluoride at temperatures of 80° to 180° C.

6. A process for the preparation of a compound of the formula (I), which comprises reacting an aryl halide of the formula

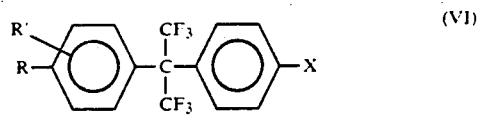

in which X is chlorine or bromine and R and R' have the meaning mentioned in formula (I) with itself in the presence of a mixture composed of a phosphine, metallic zinc and a nickel salt.

7. A compound as claimed in claim 1, wherein the lower alkyl is the group —CH₃.

8. A compound as claimed in claim 1, wherein R' is in the ortho-position relative to the radical R.

9. The process as claimed in claim 5, wherein, in method a), in terms of the ratio of (V) to (IV), the reactants are employed in a ratio of at least 1:2.

10. The process as claimed in claim 5, wherein the molar ratio of hydrogen fluoride to the compound (II) is 7:1 to 25:1.

11. The process as claimed in claim 5, wherein the reaction is carried out at 100° to 160° C.

12. The process as claimed in claim 5, wherein the reaction is carried out in 20 to 90 hours.

13. The process as claimed in claim 6, wherein the proportion of the nickel(II) salt is 1–10 mol %, that of the phosphine is 5–40 mol %, and that of the zinc is 120–160 mol %, relative to the aryl halide employed.

14. The process as claimed in claim 6, wherein the reaction is carried out at a temperature of 40° to 80° C.

15. The process as claimed in claim 6, wherein the reaction time is 2 to 8 hours.

16. A method of using the compound as claimed in claim 1 for the preparation of monomers which are employed as a component for partially fluorinated -polycondensates, in particular partially fluorinated polyesters, polyamides and polyimides.

17. The process as claimed in claim 5, wherein, in method a), in terms of the ratio of (V) to (IV), the reactants are employed in a ratio of 1:2.2 to 1:4.4.

18. The process as claimed in claim 5, wherein the molar ratio of hydrogen fluoride to the compound (II) is 10:1 to 20:1.

19. The process as claimed in claim 5, wherein the molar ratio of hydrogen fluoride to the compound (II) is 8:1 to 12:1.

20. The process as claimed in claim 5, wherein the reaction is carried out in 40 to 70 hours.

21. The process as claimed in claim 6, wherein the proportion of the nickel (II) salt is 3 to 6 mol %, that of the phosphine is 20 to 30 mol %, and that of the zinc is 120–160 mol %, relative to the aryl halide employed.

* * * * *